(12) United States Patent
Mishra et al.

(10) Patent No.: US 10,116,632 B2
(45) Date of Patent: Oct. 30, 2018

(54) SYSTEM, METHOD AND COMPUTER-ACCESSIBLE MEDIUM FOR SECURE AND COMPRESSED TRANSMISSION OF GENOMIC DATA

(71) Applicant: NEW YORK UNIVERSITY, New York, NY (US)

(72) Inventors: Bhubaneswar Mishra, Great Neck, NY (US); Jason Reed, Midlothian, VA (US)

(73) Assignee: New York University, New York, NY (US)

( * ) Notice: Subject to any disclaimer, the term of this patent is extended or adjusted under 35 U.S.C. 154(b) by 177 days.

(21) Appl. No.: 14/852,936

(22) Filed: Sep. 14, 2015

(65) Prior Publication Data
US 2016/0080528 A1     Mar. 17, 2016

Related U.S. Application Data
(60) Provisional application No. 62/049,740, filed on Sep. 12, 2014.

(51) Int. Cl.
*H04L 29/06* (2006.01)
*H04W 4/60* (2018.01)
(Continued)

(52) U.S. Cl.
CPC .......... *H04L 63/0435* (2013.01); *G06F 19/22* (2013.01); *H04L 67/10* (2013.01);
(Continued)

(58) Field of Classification Search
CPC .... H04W 4/003; H04L 67/10; H04L 63/0435; H04L 67/12; G06F 19/22; G06F 19/321
See application file for complete search history.

(56) References Cited

U.S. PATENT DOCUMENTS

| | | | |
|---|---|---|---|
| 2013/0185267 A1* | 7/2013 | Gatewood | H03M 7/3084 707/693 |
| 2013/0304391 A1* | 11/2013 | Cardonha | G06F 19/22 702/20 |

(Continued)

OTHER PUBLICATIONS

"Performance Evaluation of Storage and Retrieval of DICOM Image Content in Oracle Database 11g Using HP Blade Servers and Intel Processors," An Oracle White Paper, pp. 1-7, Jan. 2010.
(Continued)

*Primary Examiner* — Baotran N To
(74) *Attorney, Agent, or Firm* — Hunton Andrews Kurth LLP

(57) ABSTRACT

An exemplary system, method and computer-accessible medium can be provided for generating an encrypted reference-based secure-compression of randomly located short sequence reads from a genome(s), which can, for example, including obtaining information related to the randomly located short sequence reads, obtaining second information related to a plurality of reference sequences for the genome(s), generating third information related to a set of edit calls containing location information based on the first and second information using a base-calling procedure and an alignment procedure, and generating the encrypted reference-based secure-compression of the first information based on the third information. The exemplary system, method and computer-accessible medium can facilitate the exemplary chemistry box to generate analog information to be locally and physically separated from informatics box interpreting digital data.

12 Claims, 10 Drawing Sheets

(51) Int. Cl.
  *H04W 4/00*  (2018.01)
  *H04L 29/08*  (2006.01)
  *G06F 19/22*  (2011.01)
  *G06F 19/00*  (2018.01)

(52) U.S. Cl.
  CPC .............. *H04W 4/003* (2013.01); *H04W 4/60* (2018.02); *G06F 19/321* (2013.01); *H04L 67/12* (2013.01)

(56) References Cited

U.S. PATENT DOCUMENTS

2016/0070859 A1* 3/2016 Ignatenko ............... G06F 19/22 707/693
2016/0352699 A1* 12/2016 Sinclair ................... G06F 19/10

OTHER PUBLICATIONS

Bisiani, R., "Beam Search, in Encyclopedia of Artificial Intelligence," Wiley & Sons, vol. 1, pp. 56-58, 1987.

Rehm, H.L., et al., Amer Coll Med, and A. Genomics Lab Quality, ACMG clinical laboratory standards for next-generation sequencing. Genetics in Medicine, 2013. 15(9): p. 733-747.

Schrijver, I., et al., Opportunities & Challenges . . . Genome Sequencing a Report of the Association for Molecular Pathology. Jour of Molecular Diagnostics, 2012. 14(6): p. 525-540.

Shoenbill, K., et al., Genetic data and electronic health records: . . . logistical and technological considerations. Jour of the Amer Medical Info Assoc, 2014. 21(1): p. 171-180.

NSF Innovation Corps. Available from: http://www.nsf.gov/news/special_reports/i-corps/index.jsp.

Menges, F., et al., TotalReCaller: improved accuracy and performance via integrated alignment and base-calling. Bioinformatics, 2011. 27(17): p. 2330-2337.

Fritz, M.H.Y., et al., Efficient storage of high throughput DNA sequencing data using reference-based compression. Genome Research, 2011. 21(5): p. 734-740.

Deorowicz, S. and S. Grabowski, Data compression for sequencing data. Algorithms for Molecular Biology, 2013.

Masys, D.R., et al., Technical desiderata for the integration of genomic data into Electronic Health Records. Journal of Biomedical Informatics, 2012. 45(3): p. 419-422.

Li, H., et al., Project Data, The Sequence Alignment/Map format and SAMtools. Bioinformatics, 2009. 25(16): p. 2078-2079.

Land, A. and A. Doig, An Automatic Method of Solving Discrete Programming Problems. Econometrica, 1960. 28(3): p. 497-520.

Systems, S. MARS. Available from: http://www.salford-systems.com/products/mars.

DICOM. Available from: http://dicom.nema.org/.

HL7. Available from: http://www.hl7.org/.

Open PGP. Available from: http://www.pa.msu.edu/reference/pgpdoc1.html.

* cited by examiner

SYSTEM, METHOD AND COMPUTER-ACCESSIBLE MEDIUM FOR SECURE AND COMPRESSED TRANSMISSION OF GENOMIC DATA

CROSS-REFERENCE TO RELATED APPLICATION(S)

This application relates to and claims priority from U.S. Patent Application No. 62/049,740, filed on Sep. 12, 2014, the entire disclosure of which is incorporated herein by reference.

FIELD OF THE DISCLOSURE

The present disclosure relates generally to genomic data, and more specifically, to exemplary embodiments of an exemplary system, method and computer-accessible medium for secure and compressed transmission of genomic data.

BACKGROUND INFORMATION

While there is currently a desire to provide a relatively inexpensive (e.g., about $1000) genome sequencing technology of acceptable read length (e.g., about 100 bps), accuracy (e.g., one base error in about 10,000 bps) and high-speed (e.g., a turn-around time of less than about a day), it can be even more important to build the infrastructure that can facilitate the resulting data, most of which can be applied in clinical setting, to be transmitted, stored, queried and accessed as accurately, efficiently, securely and effortlessly as possible. One limiting factor to using the next generation sequencing technology for clinical purposes can be that the currently dominant genomics technologies produce data having either low accuracy or short read length, which has required additional post-processing by a remote super computer with large storage space, for example, a cloud computer. The process can have significant risks not just in terms of inaccurate data interpretation resulting in unnecessary or even disastrous clinical interventions, but also in the loss of privacy of the patient data. Exacerbating these problems, the current process incurs significant costs in transmission and storage.

Next-generation clinical sequencing is undergoing a period of incredibly rapid growth. Its applications span nearly all fields of medicine, from the prediction of drug allergies to the diagnosis of childhood diseases and guidance of cancer treatments. It has become an important tool for basic biomedical research and is seeing significant adoption in the clinical diagnosis of inherited monogenetic disorders, and the profiling of acquired and somatic mutations to guide therapeutic choice and inform prognosis in cancer. (See e.g., References 1 and 2). Emerging clinical applications of next-generation sequencing include monitoring transplant rejection and non-invasively diagnosing a variety of prenatal diseases and conditions. (See e.g., References 1 and 2). Accompanying this rapid expansion are large-scale bioinformatics challenges. The data generated by sequencers currently suffers from inefficiencies in both processing and long-term storage. This situation translates into greater error rates, higher costs and longer wait times for actionable medical information.

This problem is particularly acute for clinical sequencing laboratories as the changing regulatory landscape for healthcare, combined with variation in federal and state laws regarding medical record storage needs (see e.g., Reference 3), results in most DNA sequencing labs storing data indefinitely. With sequence data generation forecast to increase exponentially in the near future, many practitioners are concerned that a data storage crisis is looming. Surprisingly, most clinical sequencing centers abstain from compressing the sequencing data they store, primarily due to the lack of a data-secure, scalable and easy-to-use tool for sequence compression.

Thus, it may be beneficial to provide an exemplary system, method and computer-accessible medium for secure and compressed transmission of genomic data, which can overcome at least some of the deficiencies described herein above.

SUMMARY OF EXEMPLARY EMBODIMENTS

An exemplary system, method and non-transitory computer-accessible medium can be provided for generating a reference-based compression of randomly located short sequence reads from a genome(s), which can, for example, include obtaining first information related to the randomly located short sequence reads, obtaining second information related to a plurality of reference sequences for the genome(s), generating third information related to a set of edit calls containing location information based on the first information and the second information using a base-calling procedure and an alignment procedure, and generating a reference-based compression of the first information based on the third information.

In some exemplary embodiments of the present disclosure, the randomly located short sequence reads can be generated using a Sanger chemistry procedure, a sequencing-by-synthesis procedure, a sequencing-by-hybridization procedure or a sequencing-by-ligation procedure. The reference sequences can include information related to a whole-genome reference sequence of a single individual or a population. The whole-genome reference sequence can be haplotypic, genotypic, or a collection of contigs. The reference sequences can include a particular number of point-mutations, indels or structural unknown errors. The base-calling and the alignment procedures can be performed substantially concurrently. A set of data-points can be generated, each of which can contain a chromosomal location, offset and an edit-call based on the base-calling and alignment procedures. The location information can be randomly padded and encrypted using a public-key crypto procedure. The locational information can be provided in a substantially random order.

In some exemplary embodiments of the present disclosure, the analog signal(s) of the genome(s) can be generated, which can include an intensity. The reference-based compression of the first information can be encrypted, and the encrypted reference-based compression of the first information can be transmitted over a network. Differences between the first information and the second information can be determined, and the reference-based compression of the first information can be generated based on the determined differences. The second information can be stored using a Burrows-Wheeler transform with FM-index.

In a further exemplary embodiment of the exemplary disclosure, an exemplary system, method and computer-accessible medium can be provided that can, for example, obtain first information related to a plurality of securely encrypted reference-based secure-compression of short sequence read data, obtain second information related to a plurality of reference sequences, and generate at least one edit-call based on the first and second information.

These and other objects, features and advantages of the exemplary embodiments of the present disclosure will become apparent upon reading the following detailed description of the exemplary embodiments of the present disclosure, when taken in conjunction with the appended claims.

BRIEF DESCRIPTION OF THE DRAWINGS

Further objects, features and advantages of the present disclosure will become apparent from the following detailed description taken in conjunction with the accompanying Figures showing illustrative embodiments of the present disclosure, in which.

Figure 1:
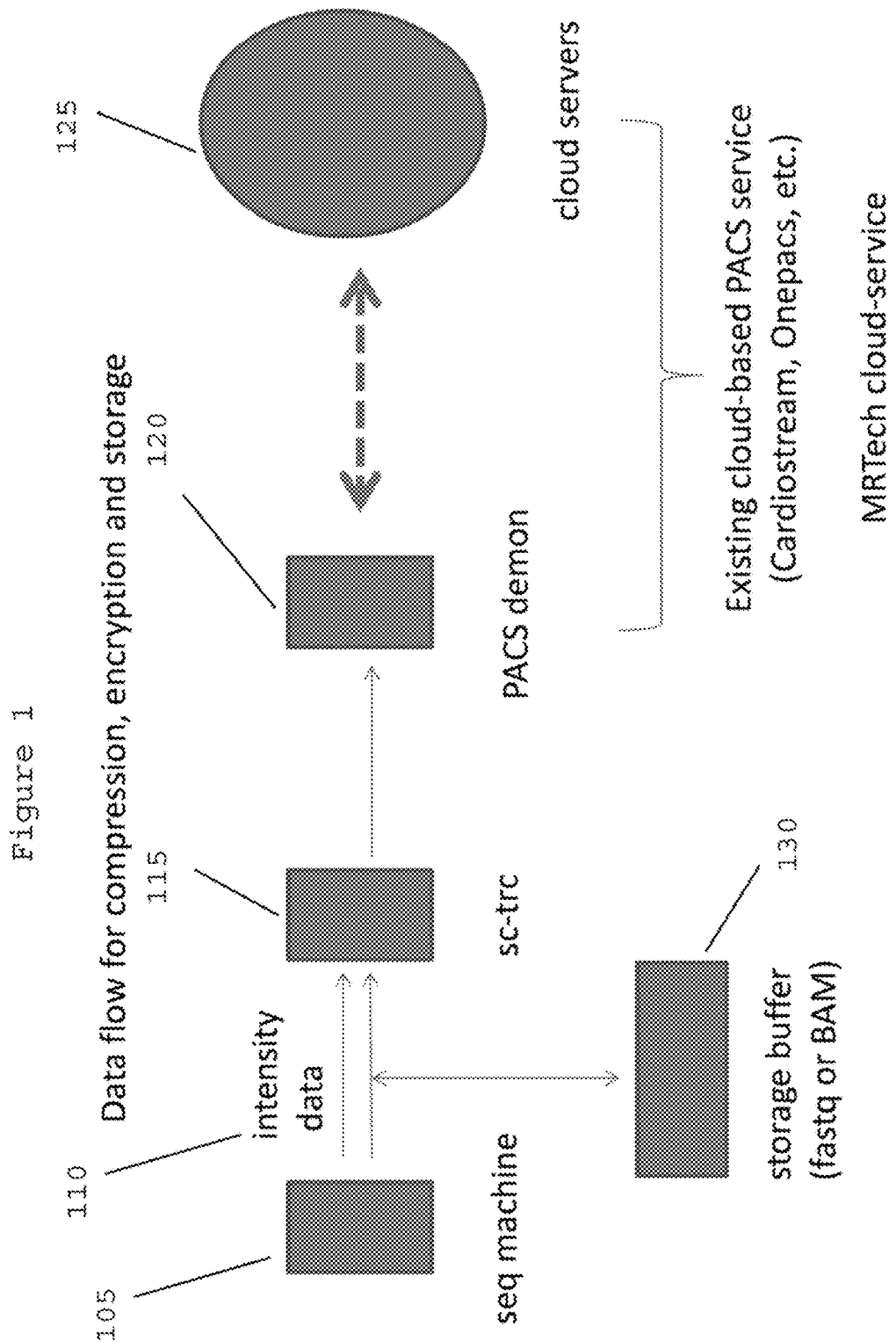
FIG. 1 is a flow diagram of a method for generating at least one compressed and secure representation of a set of short-reads obtained from a single genome according to an exemplary embodiment of the present disclosure.

Throughout the drawings, the same reference numerals and characters, unless otherwise stated, are used to denote like features, elements, components or portions of the illustrated embodiments. Moreover, while the present disclosure will now be described in detail with reference to the Figures, it is done so in connection with the illustrative embodiments and is not limited by the particular embodiments illustrated in the Figures and the accompanying claims.

DETAILED DESCRIPTION OF EXEMPLARY EMBODIMENTS

Exemplary embodiments of the present disclosure relates generally to creating a secure and compressed representation of haplotypic or genotypic genomic information including short, non-contextual, sequence-read data, as obtained by various available or anticipated sequencing technologies (e.g., Illumina/Solexa, 454, ABI-SOLID, Complete Genomics, Nanopore-based Sequencing, Pacific Biosciences, Sanger Sequencing, Sequencing-by-Synthesis, Sequencing-by-Ligation, Sequencing-by-Hybridization, etc.); additional assistance can also be sought from long-range reference-based locational and differential information (e.g., reference sequences, a population of reference sequences, etc., possibly organized as indexed data structures in its entirety or collectively as a set of contigs). The present disclosure also relates generally to communication and deanonymization of whole or partial, genomic data with or without genetic biomarkers/polymorphisms/edit-calls, for example, in methods, computer-accessible medium, and systems for transmitting and storing genomic information, which can be of clinical significance, and can be obtained at any pre-defined resolution, haplotypic ambiguity and accuracy, or can be targeted at one or more selected regions of one individual genome, or a collection of genomes (e.g., ecological sample of many bacterial genomes or genomes of collection of cells in a polyclonal tumor). This entire class of technology can be referred to as "secure and compressed storage and transmission of genomic information." The exemplary procedure underlying the present disclosure can be referred to as "SC-TRC," an acronym for Secure and Compressed Total-ReCaller.

As shown in the schematic diagram of FIG. 1, unlike the other presently available technologies, the exemplary SC-TRC 115 can target the raw analog intensity data (e.g., intensity data 110) generated by the sequencing platform (e.g., sequencing machine 105). This facilitates the exemplary system, method and computer-accessible medium to utilize Bayesian procedures and combine short-range high-accuracy sequence reads with long-rage reference genome information in order to get more accurate base-calls, more statistically significant edit-calls, more efficient reference-based data-compression, and more secure, and yet simple, encryption, which can collectively make the exemplary system, method, and computer-accessible medium agnostic as well as competitive. The intensity data 110 can be stored in storage buffer 130 (e.g., in either a FASTQ or BAM format as described below). The exemplary output from SC-TRC 115 can be input into a picture archiving and communication system (PACS") daemon 120, which can communicate with cloud servers 125 in order to store the information.

Thus, the exemplary system, method, and computer-accessible method according to the exemplary embodiment of the present disclosure can be structured to positively impact the field by: (i) abstracting away the technological complexities of data management and transmission with a new protocol, obviating need for large engineering teams in clinical labs, (ii) facilitating the data to be transmitted and stored for a longer period of time at a cheaper cost, without any privacy or cyber-security concerns, and finally, (iii) permitting third-party quality control and regulation (e.g., HIPAA compliance; (see e.g., Reference 3)) of the entire pipe-line without infringing on the privacy of the patients. The exemplary system, method and computer-accessible medium, according to an exemplary embodiment of the present disclosure, can target the clinical sequencing applications owing to its demonstrated need for increased data security and sustainable data storage, as well as its high potential for growth relative to other sequencing applications.

The National Science Foundation's I-Corps program (see e.g., Reference 4) recently conducted an interview to better understand the state of the next-generation sequencing ecosystem. After over 50 in-person interviews, it was found that clinical labs using sequencing for genetic testing: (i) valued accuracy the highest among users of next-generation sequencing, (ii) needed fast turnaround, and (iii) were concerned about the future costs of data management, storage and security (e.g., FIG. 1). Importantly, laboratory managers said that costs and data transfer times are prohibitive.

The sequencing community has recognized that memory footprint of clinical sequencing data will soon "exceed the capacity of commonly available network bandwidth and disk storage in healthcare setting." (See e.g., Reference 8). Data compression solutions can be needed to address this problem, and the most promising approach to achieve meaningful compression ratios (e.g., about 50:1 or better, depending on the genome complexity and reference quality, with the best reported value hovering around about 400:1 (see, e.g., References 6 and 7)) can be to store the differences between an individual's sequence and a universally available "clinical standard reference genome." "The current de facto standard for storing the output of high throughput sequencing platforms such as Illumina can be the "FASTQ" file, is a text-based format for storing both the individual sequence reads (e.g., the string of nucleotide bases) and the corresponding per-base "quality" scores, with a succinct single ASCII character encoding. Presently, the individual reads, after they can be aligned to a reference sequence, can be provided in the uncompressed Sequence Alignment/Map ("SAM") format (see, e.g., Reference 9) or BAM (e.g., the binary form of SAM), which can be interoperable, flexible and simple with respect to different alignment, query and retrieval software. A typical genomic sequence raw dataset (e.g., about 30× coverage, about 1,100 million individual 100 by reads) in FASTQ format can be about 250 Gb in size, and the aligned data in BAM format can be roughly about 300 Gb in size. Presently, the closest analog to genomic sequence data in healthcare can be image sets derived from various modalities (e.g., CT scans, ultrasound, etc.), which can be stored in compressed form, and securely managed using a dedicated server and network infrastructure. These medical image datasets typically range in size from about 0.01 Gb to about 5 Gb (see, e.g., Reference 10); therefore, about 100× compression of an about 300 Gb BAM file into an about 3 Gb file would result in a data object of similar size.

In existing sequencing bioinformatics pipeline, the software tools used in each of its phases may not be standardized, and can often take the form of a serial pipeline of open-source and homemade tools specific to the laboratory using them. In certain clinical applications, the exemplary system, method, and computer-accessible medium, according to an exemplary embodiment of the present disclosure, can also be combined with the upstream portion of an extant pipeline, which can be normally used for the sequence generation and low-level analysis, though it operating solely has significant beneficial impacts on the time and data storage capacity when used as is.

Figure 2:
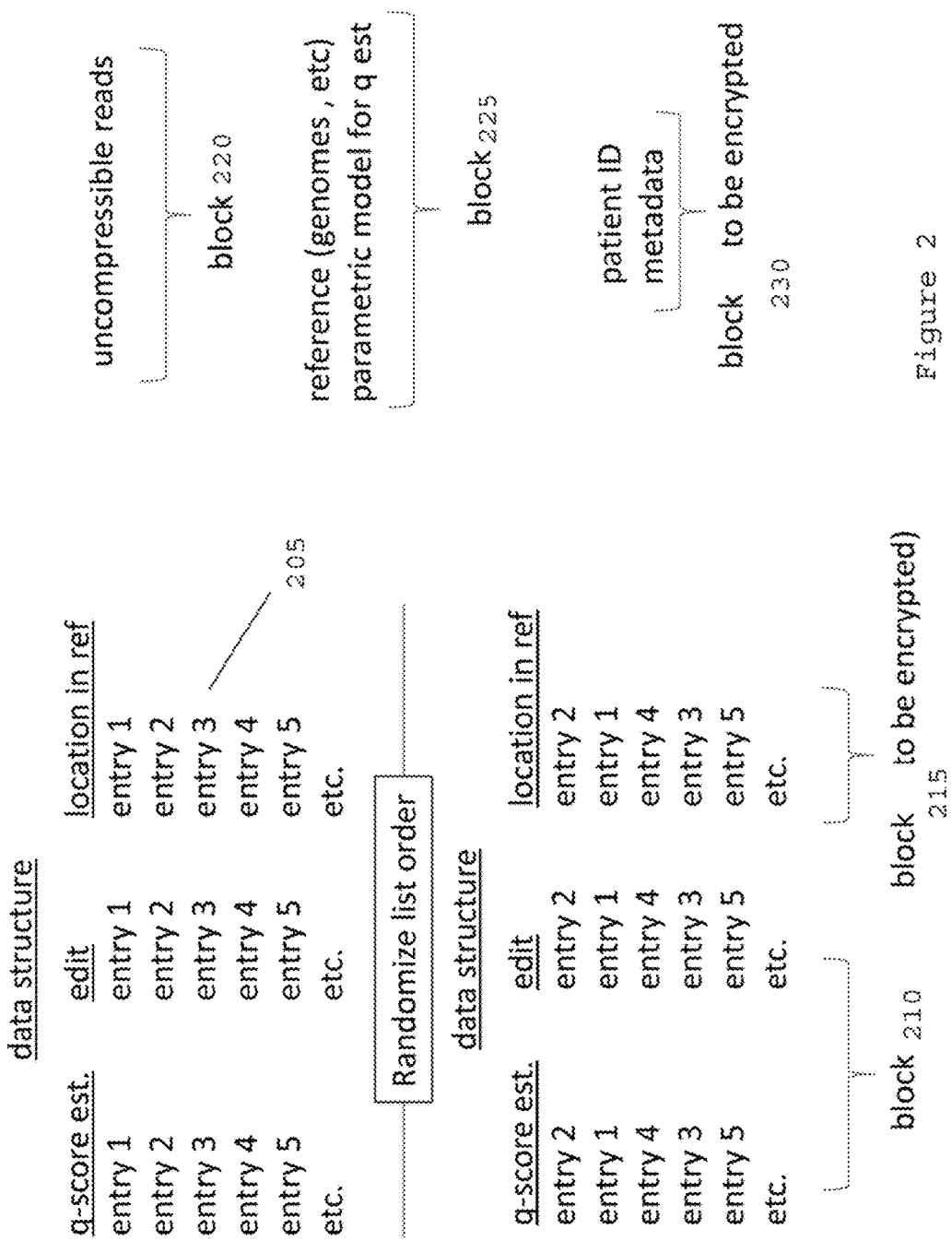
FIG. 2 is a combination of a system and a further flow diagram for generating at least one compressed and secure representation of a set of short-reads according to an exemplary embodiment of the present disclosure.

For example, as shown in FIG. 2, the exemplary q-score estimate, the edit call, and the location the reference (e.g., block 205) can be in a randomized order. The data structure can then be ordered, for example, the q-score estimate and the edit call in block 210, and the location in the reference (e.g., to be encrypted) in block 215. Uncompressible reads (e.g., block 220 can also be included in combination with the reference parametric model for q-score estimation (e.g., block 225) and the patient ID and metadata (e.g., block 230, which can be encrypted). All of the above can be transmitted over a network or stored locally.

Figures 3A, 3B:
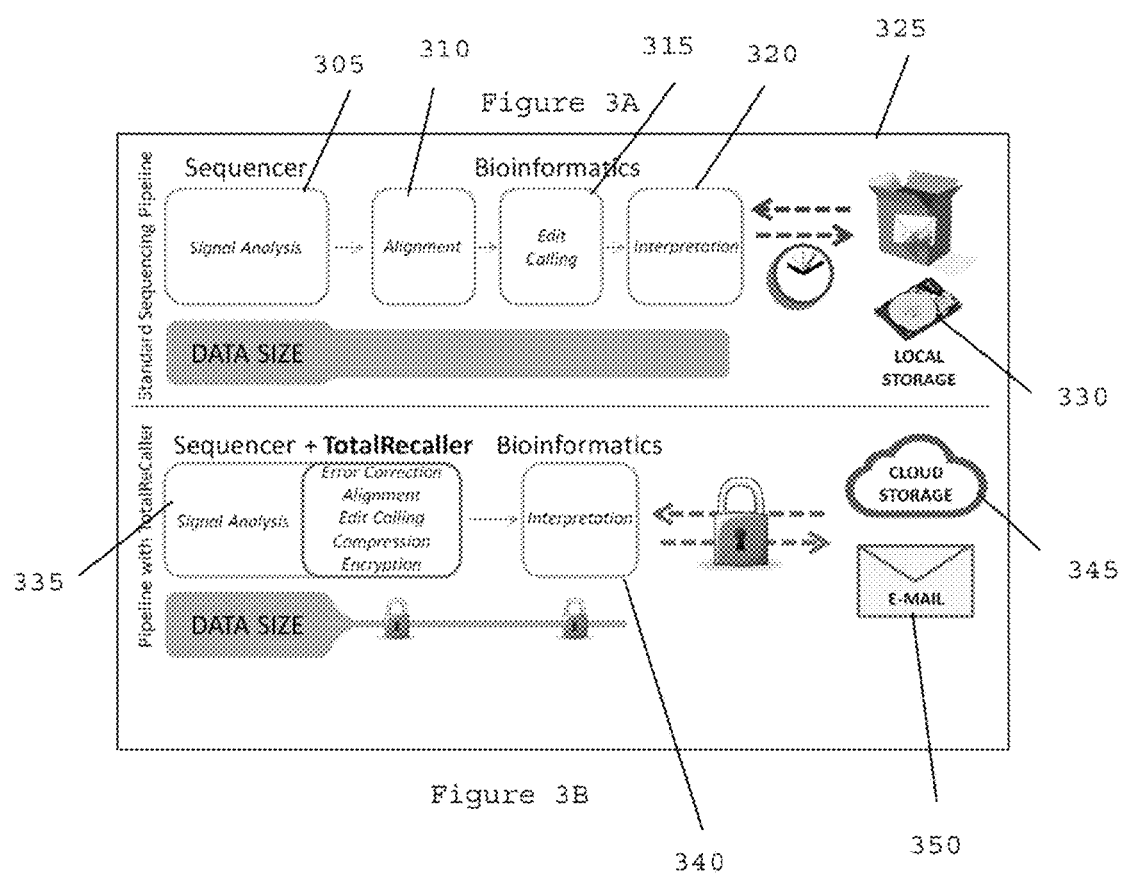
FIG. 3A is an exemplary diagram illustrating bioinformatics pipelines using standard tools.
FIG. 3B is an exemplary diagram illustrating bioinformatics pipelines using the exemplary Total Recaller according to an exemplary embodiment of the present disclosure.

For example, as shown in exemplary flow diagram of FIG. 3A, existing sequence bioinformatics pipelines can first perform a sequence analysis 305, and then perform an alignment at procedure 310, an edit call at procedure 315, and an interpretation at procedure 320. This information can then either be stored locally in local storage 330 and/or transmitted as packet switching data 325. In contrast, the exemplary system, method and computer-accessible medium, according to an exemplary embodiment of the present disclosure, can perform a signal analysis at procedure 335, which can include an error correction, an alignment, an edit call, compression, and encryption. Then, at procedure 340, and interpretation can be performed, and the exemplary output can be provided to a cloud storage 345 and/or through file transfer 350.

Today's next-generation sequencing pipelines can be highly heterogeneous, and can be designed to generate and process nucleic acid sequences for a variety of downstream uses. These can include multi-organism whole genome sequencing, gene-specific or region-specific targeted sequencing, and sequence-based gene expression profiling. This variety can utilize the implementation of unique assortments of bioinformatics tools, including enterprise, open-source, and home-grown software and hardware solutions. The bioinformatics pipeline landscape can be dominated by academic research-oriented solutions and may not be optimized for clinical sequencing, which represents only a small, but fast-growing fraction of total sequencing activity.

Clinical sequencing faces a number of data management challenges: (i) the data generated from current clinical pipelines has a larger digital footprint than can be sustainable, (ii) it suffers from long turnaround times, (iii) it faces high costs of storage and transfer and (iv) there may be no consensus process to implement data security. Research has found that presently, clinical sequencing data may not be stored conveniently on cloud servers due to privacy and cost concerns, and can often be physically mailed on hard disks. In the end, clinicians wait longer and patients pay more for data of lower quality.

The exemplary system, method, and computer-accessible medium, according to an exemplary embodiment of the present disclosure, can utilize the fact that its read alignment process can be used to compresses the sequence information by storing only the location of the read within the reference genome, and recording any detected differences between the read and the reference. The exemplary procedure of the exemplary system, method, and computer-accessible medium can provide high compression ratios (e.g., over about 50:1 in an embodiment using TotalRecaller (see e.g., Reference 6 and 7)) in applications such as human clinical sequencing, where the reference genome can be very well annotated. Little information can be lost in this process, and the sequence set can be re-queried as new medically actionable sequence variants can be discovered, as is current practice.

The exemplary result can be days-faster delivery of information to physicians with more than an order of magnitude increase in usable storage space, which can lower costs and speed-up diagnosis and treatment of patients. The exemplary reduction in the size of sequence data can also remove barriers to more flexible cloud-based storage solutions, democratizing next-generation sequencing for smaller laboratories and hospitals.

The exemplary TotalRecaller can be included at the very beginning of the sequencing process to address these issues. As a combination hardware and software package, it can employ procedures that can: (i) decrease error rates, (ii)

decrease turnaround time, and (iii) compress data to smaller than 1/50th its original size in a Health Insurance Portability and Accountability Act ("HIPAA")-compliant encrypted form. The exemplary end result can be days-faster delivery of information to physicians with more than an order of magnitude increase in usable storage space, lowering costs and speeding diagnosis and treatment of patients. The encryption and compression of data can also remove barriers to more flexible cloud-based storage solutions, democratizing next-generation sequencing for smaller laboratories and hospitals.

Typical next-generation bioinformatics pipeline operates in three distinct phases: (i) sequence generation/low-level analysis, (ii) high-level data interpretation and (iii) data archiving (e.g., see FIG. 2). The software tools used in each of these phases may not be standardized, and can often take the form of a serial pipeline of open-source and homemade tools specific to the laboratory using them. The exemplary TotalRecaller ("TRC") can function at the upstream portion of the pipeline (e.g., sequence generation and low level analysis), but has significant beneficial impacts on the time and data storage capacity needed to implement the latter two phases.

TRC can Decrease Sequencing Errors Existing approaches use manufacturer-supplied software to classify raw analog signals generated by the sequencing machine, most often optical fluorescent intensity signals containing four colors, into one of four categories representing a specific nucleotide base, A, C, G or T. The process can be known as "base calling." TRC can use knowledge of the organism being sequenced as part of the base calling process. This can have the practical result of facilitating TRC to correctly call bases in cases where the analog data can be of lower quality and existing base callers fail to produce a correct call or, more commonly, label the base as "uncalled." It has been shown that the exemplary TotalRecaller can reduce the occurrence of errors and uncalled bases in an about 100-150 base pair sequence read by about 25%-40% as compared to the industry standard base caller, Bustard (Illumina). (See e.g., Reference 5). Due to the nature of the next-generation sequencing process, errors and uncalled bases cluster at the end of sequencing reads can increase with frequency nonlinearly as the number of bases increases. Therefore, reads produced by TotalRecaller can have the very desirable characteristic of being effectively longer by about >25% than the identical reads processed by Bustard or similar base callers. Lengthening reads can decrease the occurrence of alignment errors, which can result in higher fidelity variant calls, and has been shown to increase compression ratios in referential compression schemes, such as those used by TRC. (See e.g., Reference 6).

TRC Can Shorten Turnaround Time. TotalRecaller can compute base calls and sequence alignments simultaneously, which can avoid the need for the separate downstream alignment process that existing pipelines now use. TRC's alignment procedures are fast and scalable enough to operate in real-time. In addition, TRC's output includes a list of non-interpreted variants (e.g., SNPs and short indels) from the reference sequence (e.g., currently, human genome hg19), which can save time by reducing the utilized number of additional low-level variant calling procedures.

TRC Can Reduce Data Storage Requirements and Improve Security. Sequence data may not typically be compressed by laboratories, either at the time of generation or after analysis. In some cases, generalized tools, not specifically designed for sequencing (e.g., such as gZip), can be used to achieve local compression of at most 3-4 fold.

(See e.g., Reference 7). The read alignment process of TRC can be used to compress sequence information by storing only the location of the read within the reference genome, and by recording any detected differences between the read and the reference. This exemplary procedure can yield very high compression ratios (e.g., over 50:1 for TotalRecaller) (see e.g., References 6 and 7) in applications such as human clinical sequencing, where the reference genome can be very well annotated.

It has been previously hypothesized that, in re-sequencing applications, the error rates of next-generation sequencing can be reduced substantially by using information about the genome being sequenced. Studies were conducted that quantitated the error correction magnitude and measured the false-negative and false-positive rates associated with this exemplary method. (See e.g., Reference 5). Sequence reads were obtained from Illumina GAIIx and HiSeq 2500 machines for four organisms (e.g., phiX, E. Coli, V. Cholera, and P. trichocarpa). It was determined that the exemplary error correction approach, in the context of genome re-sequencing, demonstrated about a 25-50% reduction in average error rates for about 100-150 bp reads. For typical values of weighting parameters, the SNP specificity (e.g., rate of calling a true SNP instead of an erroneous base-calls) and SNP sensitivity (e.g., rate of calling a SNP relative to all true SNPs) were perfect up to the first about 60 cycles, better than about 99% for the first about 80 cycles, and degrading by another about 1-3% by the about 120th cycle on phiX, E. Coli and V. Cholera reads. Values degraded to about 95% for P. trichocarpa, for which a correct reference had not yet been fully assembled.

TRC's error correction procedure can support real-time edit calling (e.g., differences from the aligned subsequence of a reference). This capability can be used to create a single TRC product that can simultaneously correct sequencing errors, perform non-interpreted variant identification, and compress and encrypt data so that it can be archived and transmitted securely.

The exemplary system, method, and computer-accessible medium, according to an exemplary embodiment of the present disclosure, can integrate a combination hardware package (e.g., chemistry and computation) and a software package/program for sequencing DNA, genomes or transcriptomes, which: (i) can decrease error rates, (ii) can decrease turnaround time, and (iii) can compress data to smaller than about 1/50th its original size in a HIPAA-compliant encrypted form.

Existing approaches use manufacturer-supplied software to classify raw analog signals generated by the sequencing machine, which are most often optical fluorescent intensity signals containing four colors, into one of four categories representing a specific nucleotide base, A, C, G or T. The process is known as "base calling". The exemplary TotalRecaller base calling procedure can use knowledge of the organism being sequenced as part of the base calling process. Such knowledge can facilitate TotalRecaller to calculate the probability that any specific analog signal corresponds to an A, C, G or T, using information about the frequency of occurrence of that base in the genome, and the frequency with which the base would be expected to follow previously called bases in a sequence read. This strategy has the practical result of facilitating TotalRecaller to correctly call bases in cases where the analog data can be of lower quality and where existing base callers fail to produce a correct call, or more commonly, label the base as "uncalled". It has been demonstrated that TotalRecaller can reduce the errors and uncalled bases in a 100-150 base pair sequence read by about 25%-40% as compared to the industry standard base caller, Bustard (e.g., Illumina). (See e.g., Reference 5). By the nature of the next-generation sequencing process, the errors and uncalled bases cluster at the end of the read, increase nonlinearly with frequency as the number of bases increases. Therefore, reads produced by the exemplary TotalRecaller have the very desirable characteristic of being effectively longer by about >25% than the identical reads processed by Bustard or similar base callers, because the 'quality' of the bases in the tail (e.g., last about 25%) of TotalRecaller-determined reads generally exceed standard minimum quality thresholds, whereas those produced by the other software do not.

TotalRecaller can compute or otherwise determine (e.g., via a computer processor) base calls and sequence alignments in one atomic single computational step, which can avoid the need for the separate downstream alignment process that all existing pipelines now utilized. The exemplary TRC has achieved a technical breakthrough by making TRC's alignment algorithms fast and scalable enough to operate in real-time. TRC's output includes a list of non-interpreted variants from the reference sequence (e.g., currently, human genome hg19), which can be interpreted for clinical relevance without additional low-level variant calling procedures being utilized.

Sequence data may not typically be compressed by laboratories, either at the time of generation or after analysis. In some cases, generalized tools not designed specifically for sequencing, such as gZip, can be used to achieve local compression of at most about 3-4 fold. (See e.g., Reference 6). The exemplary system, method, and computer-accessible medium, according to an exemplary embodiment of the present disclosure, can utilize the fact that its read alignment process can be used to compresses the sequence information by storing only the location of the read within the reference genome, and recording any detected differences between the read and the reference.

Figure 4:
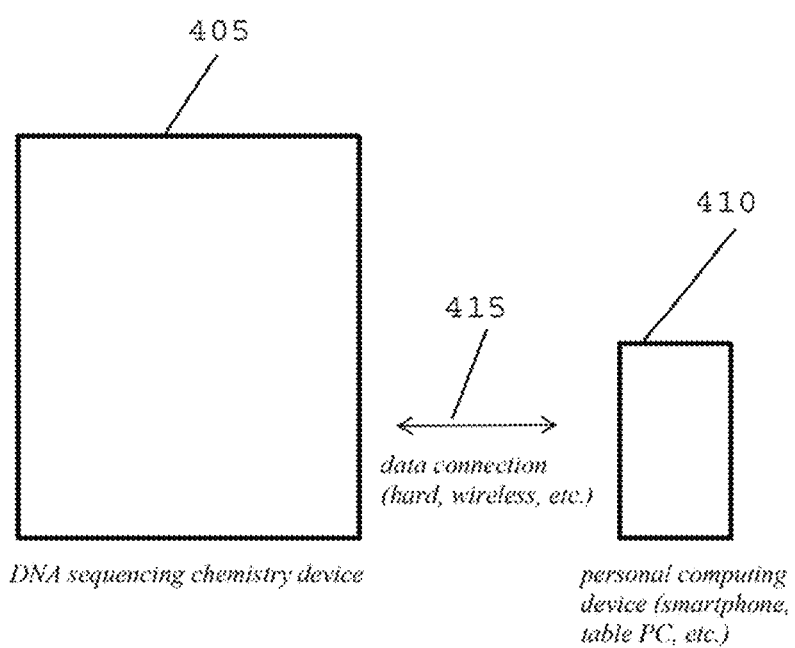
FIG. 4 is block diagram of an exemplary DNA sequencing device connected to an exemplary computing device according to an exemplary embodiment of the present disclosure.

As illustrated in FIG. 4, the exemplary system, method, and computer-accessible medium, according to an exemplary embodiment of the present disclosure, can include a chemistry-box (e.g., DNA Sequencing Chemistry Device 305) that can generate interpretable analog signals (e.g., either per base of the DNA or per tiled k-mers along the DNA) coupled to a separate small portable computational device (e.g., a desktop, a tablet or a smartphone 310) over data connection 315, which can achieve in one single undivided operation, alignment to genome reference(s), base-call, edit-call, variant-call, variant interpretation, data-compression and data-encryption and then securely store (e.g., locally and/or remotely) the encrypted-compressed genomic data with needed annotation of the alignment and quality scores in such a manner that the data can be decrypted and uncompressed, as needed, in the future.

Figure 5:
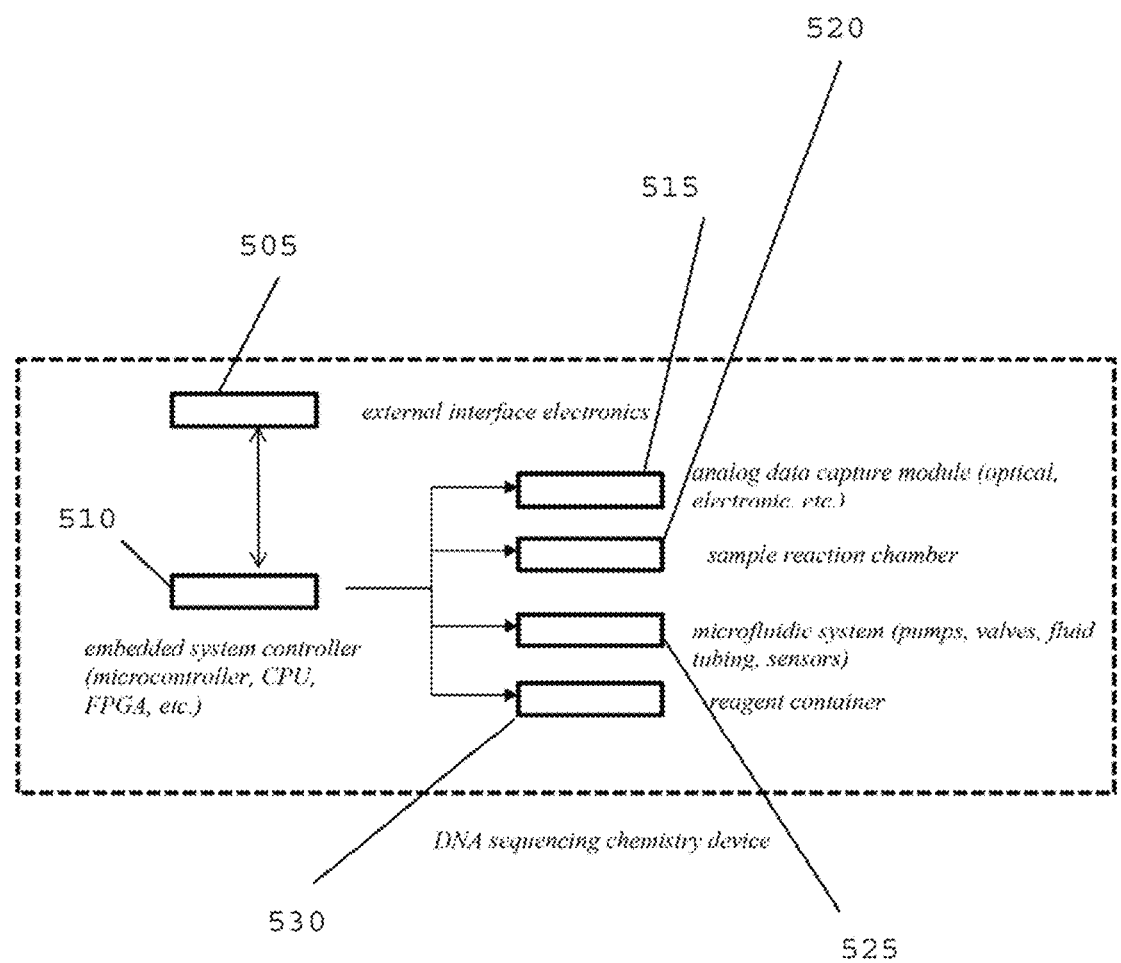
FIG. 5 is an exemplary block diagram of an exemplary DNA sequencing chemistry device according to an exemplary embodiment of the present disclosure.

FIG. 5 illustrates the exemplary DNA Sequencing Chemistry Device 305 shown in FIG. 4. For example, as shown in FIG. 4, DNA Sequencing Chemistry Device 305 can include an external interface 505, which can interface and/or interact with other electronic devices. External interface device 505 can be connected to and/or in communication with an embedded system controller 510, which can include a microcontroller, a central processing unit, a field-programmable gate array, or any other suitable controller. Embedded system controller 510 can be connected to and/or in communication with an analog data capture module 515, a sample reaction chamber 520, a microfluidic system 525 and/or a reagent container 530.

The exemplary system, method, and computer-accessible medium according to an exemplary embodiment of the present disclosure can yield very high compression ratios (e.g., over about 50:1 using TotalRecaller) (see, e.g., References 6 and 7) in applications such as human clinical sequencing where the reference genome can be very well annotated. Little information can be lost in this exemplary process, and the exemplary sequence set can be re-queried as new medically actionable sequence variants can be discovered, as is current practice.

Thus, in re-sequencing applications, the exemplary system, method, and computer-accessible medium according to an exemplary embodiment of the present disclosure can reduce the error rates of next-generation sequencing by using information about the genome being sequenced. Significant improvement using the exemplary system, method and computer-accessible medium has been demonstrated by studies that quantitated the error correction magnitude, and measured the false-negative and false-positive rates associated therewith. (See e.g., Reference 5). Sequence reads were obtained from Illumina GAIIx and HiSeq 2500 machines for four organisms (e.g., phiX, E. Coli, V. Cholera and poplar). The exemplary system, method, and computer-accessible medium's error correction approach, in the context of genome re-sequencing, has been estimated to result in a about 25-50% reduction in average error rates for about 100-150 bp reads. For typical values of weighting parameters, the SNP specificity (e.g., rate of calling a true SNP instead of an erroneous base-calls) and SNP sensitivity (e.g., rate of calling a SNP relative to all true SNPs) were perfect up to about the first 60 cycles, better than about 99% for about the first 80 cycles and degrading by about another 1-3% by about the 120th cycle on phiX, E. Coli and V. Cholera reads; the numbers degraded to about 95% for poplar genome, for which correct reference had not been fully assembled.

The exemplary system, method, and computer-accessible medium according to an exemplary embodiment of the present disclosure which uses an exemplary error correction procedure can support real time edit calling (e.g., differences from the aligned subsequence of a reference), from which reference-based data compression can be a desirable extension. Thus, the exemplary system, method and computer-accessible medium, according to an exemplary embodiment of the present disclosure of this invention can be to harness this capability and create a single product which can simultaneously correct sequencing errors, perform non-interpreted variant identification, and compress and encrypt the data so it can be archived and transmitted securely.

The exemplary system, method, and computer-accessible medium, according to an exemplary embodiment of the present disclosure, can optimize Bayesian scores to perform base calling, where the score can be a function of both raw analog intensity data (e.g., from four color channels) and its hypothesized next "edit" (e.g., which could be a base: A, T, C, G, an insertion, a deletion, or a "'gap'") relative to the reference genome. The reference can be stored using a Burrows-Wheeler transform ("BWT") with FM-index, in order to use a small memory footprint without incurring a high cost in accessing and searching the reference. The composite score can be a linear combination of an intensity-based score with a weighted "edit" score/penalty, where the weight can be context-dependent, and can be optimized empirically (e.g., to optimally trade-off false-positive and negative errors). The optimization can be performed by an exemplary branch-and-bound procedure operating on a 7-ary tree (e.g., this branching factor comes from the seven different edit-operations). The scores computed at the nodes of the 7-ary tree can provide the quality score of each base-call, and can follow statistical distributions (e.g., dependent on the position and base-composition) that can be parametrically modeled; such a parametric model can be used efficiently in transmitting the quality scores with good compression and low information loss.

In order to optimize the compression, the exemplary system, method and computer-accessible medium, according to an exemplary embodiment of the present disclosure, can utilize collected statistics on the benchmark datasets as each embodiment's internal parameters can be varied in small increments over their respective ranges. The internal parameters can correspond to those used to describe multiple weighting functions (e.g., with exponential, linear and constant profiles) as well as to memory bounds, beam-width and pruning parameters (e.g., in the beam-search and branch-and-bound procedures. (See e.g., References 11 and 12). Some of the statistics can be collected over non-overlapping genomic intervals, and can consist of local genome coverage, size of the compressed output and number of errors in the recovered decompressed sequence. The exemplary system, method, and computer-accessible medium, according to an exemplary embodiment of the present disclosure, can then optimize parameters separately for average coverages of about 30× (e.g., similar to whole genome sequencing), about 100× (e.g., similar to exome sequencing) and about 1000× (e.g., similar to tumor sequencing, where allele frequencies can be about <50% due to tissue heterogeneity). Optimal exemplary values of the parameters which can lead to the best average compression (e.g., for a fixed coverage level and threshold for errors), can also be obtained by an exhaustive grid search over the parameter space. However, conducting the about 1000× optimization can facilitate a user to compare results to existing compression studies more directly, and can serve as a baseline where a user wishes to optimize for heterogeneous tumor samples.

The exemplary quality score/value in FASTQ or SAM format can be an integer mapping of the odds p/(1−p), where the probability p can correspond to the event that a base call can be incorrect. For each specific instrument platform, the quality score parameterization can be determined empirically. For compression purposes, the quality score information can be sent by parametric structures of the quality score distributions and deviations at the edit-call positions. For this purpose, the quality score distribution can be learned by an exemplary logistic regression procedure, where logit(p) can be expressed as a linear function of the position, base-value and the overall score computed for that read. The exemplary, system, method and computer-accessible medium, according to an exemplary embodiment of the present disclosure can also apply other nonlinear and more complex models (e.g., Multivariate Adaptive Regression Splines ("MARS") (see, e.g., Reference 13) or Deep Learning) to explore possible further improvements. In this exemplary procedure, some information can be lost. However, this loss is not expected to significantly affect the base calling step when using Illumina data, given its generally good quality. Such information loss could become more important when extending the approach to lower quality platforms (e.g., Ion Torrent).

In order to provide an optimal referential compression, the exemplary system, method, and computer-accessible according to an exemplary embodiment of the present disclosure can use the top-scoring alignment (e.g., or two if there can be a "tie" in their scores). It can be efficient to simply abandon the read if there can be more than two alignments that have roughly equal score, as that can be an indication of a poor quality low-value read. Such unaligned reads can be post processed into contig, and can be sent separately as a supplement. (See e.g., Reference 9). Since all the core base-calling and alignment software modules can already be possessed (see e.g., Reference 5), much of the work can be on calibrating, parameter-tuning and optimizing compressibility using the empirical analysis described above.

Since not all edit-calls can be equi-probable, and since there can be haplotypic phasing among the neighboring edit-calls, further compression of the output from the exemplary system, method, and computer-accessible medium can be achieved by using an entropic compression such as Huffman coding or even, arithmetic coding. Thus, the exemplary system, method and computer-accessible medium, according to an exemplary embodiment of the present disclosure, can incorporate standard procedures known in the literature (e.g. libhuffman, an open source version in C), and can recalibrate the empirically optimized parameters. Since typical referential compression can be expected to yield about a 50:1 compression ratio, (see, e.g., Reference 7), a user can aim for another factor of about 2 or more improvements with this exemplary strategy.

Decompressing the sequence at the receiver site can use the procedure involving following: (i) the decompressor can first compute the alignment with the stored reference using the BWT data structure and FM-indices, (ii) next, it reconstructs the appropriate "referential string," and, using the associated score parameters, generates a "synthetic quality values:" (e.g., by using a Bayesian prior that can be trained to find the "quality" as a function of the position, base-properties: purine-pyrimidine or A, T, C, G, or N, score, etc.), and (iii) the, receiver's decompressor can update the "referential string" by the edit-calls, and the associated quality scores, to create a FASTQ read, which can be appended to the SAM/BAM format output. The first two exemplary procedures can use query-retrieval operations on the reference sequence, and the last step can be implemented using known string operation procedures.

In order for the exemplary system, method and computer-accessible medium to be suitable for clinical genomics, it can need to handle the data in a manner compliant with various regulatory constraints covering patients' rights, privacy, anonymity and informed consent. (See e.g., References 3 and 8). For example, HIPAA, and its related provisions, utilized the establishment of national standards for electronic health care transactions and requirements to protect participant's health information. Also, recently, the Center for Devices and Radiological Health, at the FDA, issued a guidance document for manufacturers on cyber security of networked medical devices that use off-the-shelf software. It can be noted that the embodiment described here can be based on the current Digital Imaging and Communications in Medicine ("DICOM") and Health Level Seven International ("HL7") standards that can be commonly used in handling and encrypting medical imaging data, as well as integrated with Electronic Medical Records. (See e.g., References 14 and 15).

Exemplary Encryption

The exemplary system, method, and computer-accessible medium, according the an exemplary embodiment of the present disclosure can implement a strong privacy, public-key crypto system based on OpenPGP, which can be a standard for encrypting and decrypting data, and which has been embodied in PGP data encryption software. (See e.g., Reference 16). PGP can be widely used for signing, encrypting and decrypting texts, e-mails, files, directories and whole disk partitions. It can be considered extremely reliable, as it can be built upon rigorous mathematical theory and it has successfully withstood various cryptanalysis challenges over its lifetime. Software libraries written in C++ needed to implement open source PGP can be obtained from the PGP website. (See e.g., Reference 16). In public-key cryptography, each participant possesses two separate (e.g., but mathematically linked) keys, one of which can be private (e.g., in this case available only to the patient and the healthcare provider) and/or one publicly available (e.g., available to sequence data producers, such as clinical labs, or archival services). The public key can be used to encrypt plaintext, or to verify the data's digital signature; whereas the private key can be used to decrypt ciphertext or to create the digital signature.

An exemplary data producer (e.g., sequencing platform) can know any receiver's (e.g., cloud storage) public key, and can use it to hide the sequence read chromosomal locational, quality-score information and edit-call information (e.g., which SNP, Indel, etc.). Since the same locational information can typically be shared by more than one edit-call (e.g., all the base-differences in the same read share same chromosomal location), each time a read location can be encrypted, it can be randomly padded and given a random time-stamp, which can indicate when the sender intends to transmit that edit-call. Since the data-packets can be sent in a random order, the order of the edit-calls along the genome for a particular patient cannot be inferred, lest an eavesdropper intends to launch an attack that uses haplotype phasing to de-anonymize the patient. Once the healthcare provider (e.g., with a private key) decodes the locations, they can create the "referential string" and the edit-calls earlier.

Figure 6:
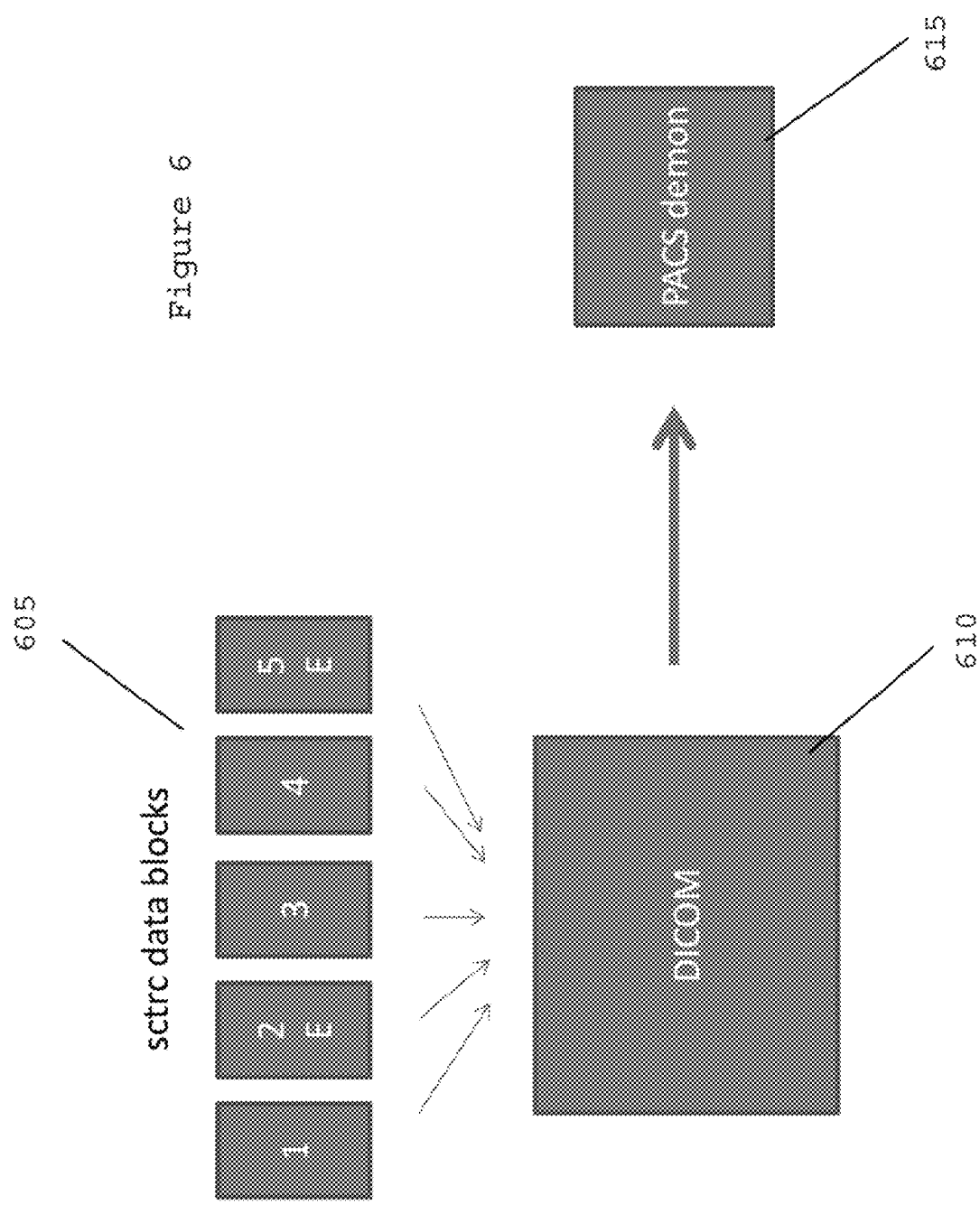
FIG. 6 is an exemplary diagram of exemplary encrypted sequence data according to an exemplary embodiment of the present disclosure.

DICOM can be the standard for the communication and management of medical imaging information and related data, created and managed by the NEMA. DICOM can be an ideal storage format for the compressed sequence data, which, can have a data footprint similar to that of medical image sets. The DICOM standard can already be integrated into HIPAA-compliant network solutions, and standard methods to link DICOM-encoded data to a patient's EHR have been established. (See e.g., Reference 3). The DICOM standard can be obtained from the open source documentation available from NEMA. (See e.g., Reference 14). DICOM specifies how devices claiming conformance to the Standard react to commands and data being exchanged, and contains explicit support not only for images and graphics but also other data objects—in this case DNA/genomic sequence data. It can also specify an established technique for uniquely identifying any data object, which can facilitate unambiguous definitions of relationships between data objects as they can be acted upon across the network. The exemplary system, method and computer-accessible medium, according to an exemplary embodiment of the present disclosure can utilize software to place the compressed and encrypted clinical genomics data with embedded anonymized patient ID tag and other simulated clinical attributes (e.g., meta data) into a DICOM file format. In preparation for making these files transferable to hospital archival servers, it can be beneficial to validate the exchangeability using TCP/IP protocol between in-house servers. It can be noted that DICOM files themselves can be further encrypted, as deemed beneficial. As shown in the schematic diagram of FIG. 6, the exemplary system, method and computer-accessible medium can compress and encrypt the exemplary SC-TRC data blocks 605 into the DICOM file format 610 before providing the information to the PACS daemon 615.

Figure 7:
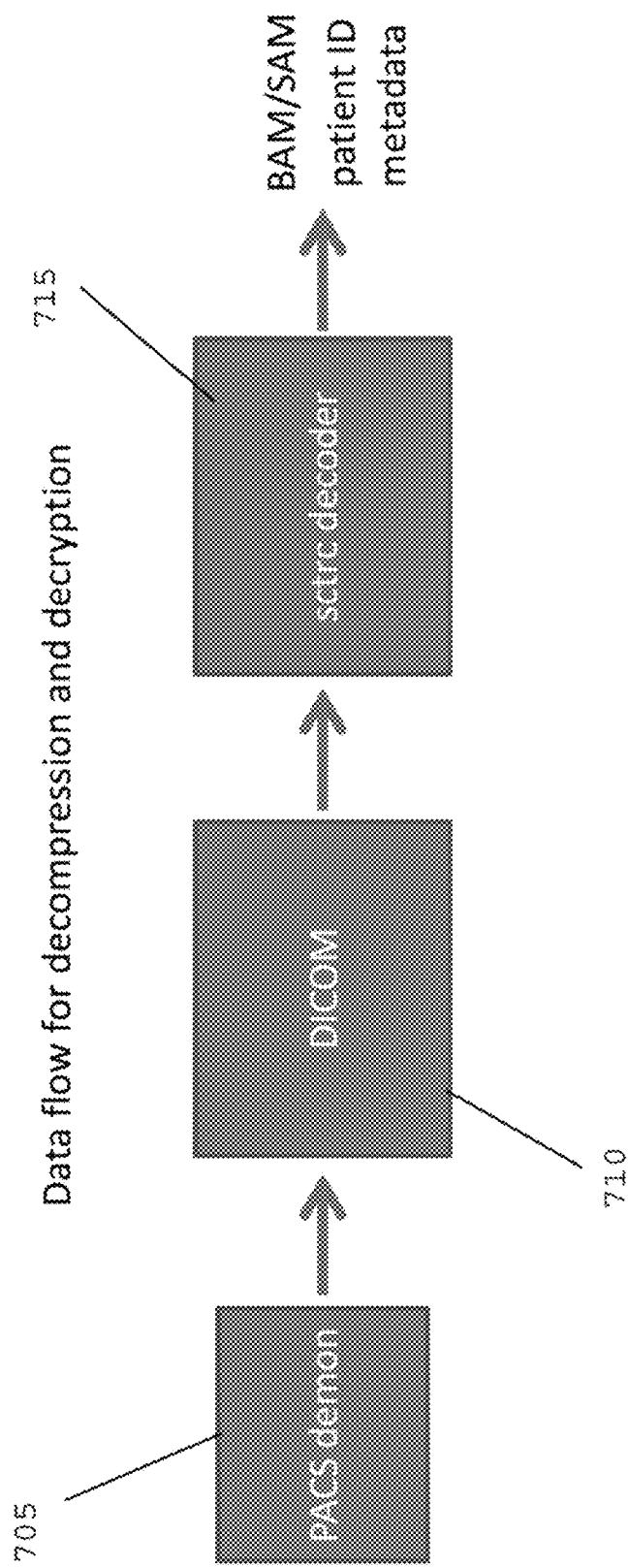
FIG. 7 is flow diagram for the decompression and decryption of exemplary metadata according to an exemplary embodiment of the present disclosure.

It has been determined, according to an exemplary embodiment of the present disclosure, that reference-based Bayesian base-calling can also be used to produce compressed and secure storage, transmission, query and access of clinical genomic data, occurring usually in the form of high coverage short sequence reads arising, not exclusively, from a diverse group of new generation sequencing technologies. Accordingly, provided herein are exemplary methods, computer-accessible medium, and systems for secure and compressed transmission of genetic data that use a single (e.g., or plurality) of reference genome(s) to act as a Bayesian prior. These exemplary methods, computer-accessible medium, and systems can provide powerful strategies that can be configured to statistically combine disparate genomic information, and novel chemical protocols that can, in parallel, manipulate and interrogate a large amount of sequencing, mapping and disease association data in various environments (e.g., personalized medicine, population studies, clinical studies, pharmacogenomics, etc.). As shown in the schematic diagram of FIG. 7, in order to decompress and decrypt the exemplary information, the exemplary system, method and computer-accessible medium, according to an exemplary embodiment of the present disclosure, can receive the information from the PACS daemon 705, provide it to the DICOM 710, and then decode the information using SC-TRC decoder 715. The exemplary information can include the BAM and/or SAM, as well as a patient ID and metadata.

Exemplary embodiments of methods, computer-accessible medium and systems for securely transmitting short-range sequence reads with assistance from long-range reference genome data to provide high compression can be used in cataloging various disease markers. Various exemplary applications of such methods, computer-accessible medium and systems can include analyzing patient genomes to predict susceptibility to various genetic or genomic diseases, or analyzing patient genomes to diagnose genomic instability and mutations as the basis of cancer. The exemplary embodiments of the present disclosure can also have agricultural and biomedical applications in drug-or-vaccine discovery, understanding behavior of a cell in an altered state (e.g., cancer, neuron-degeneration, or auto-immune disease, etc.) genetically modifying a natural wild-type organism, genetic engineering, etc. Other exemplary applications can include understanding neural behavior, evolutionary processes, and genome evolution and aging.

According to another exemplary embodiment of the present disclosure, an exemplary computer-accessible medium can be provided having stored thereon computer executable instructions for securely transmitting clinical genomic data with a high degree of data compression. When the executable instructions can be executed by a processing arrangement, such instructions configure the processing arrangement to (i) obtain a plurality of short-range sequence-reads, (ii) obtain a plurality of reference genomic information, for example, single or multiple reference, possibly in the form of multiple contigs and (ii) organize short-range sequence read information in relative positional arrangements with respect to the long-range reference sequence information to obtain compressed, and possibly encrypted, representation of the short-reads, to be stored or transmitted efficiently and securely.

Exemplary Generating Reference Sequencing Data from Targeted Cancer Panels

For development, testing and validation purposes, a set of representative clinical sequence data sets can be obtained, which can include the intensity files (e.g., .CIF) used by TRC. For instance, Ambry's breast cancer panel, Breast-Next, can be used, which targets 18 breast cancer-related genes, sequenced to a depth of about 800-1000×, and can obtain data from five breast cancer cell lines (e.g., HCC2218, BT474, HCC1395, HCC1599 and HCC1954).

Exemplary Implementation of Compression and Decompression Software

In order to provide optimal referential compression, TRC can optionally only send the top-scoring alignment (e.g., or two if there can be a "tie" in their scores). A read can be abandoned if there can be more than two alignments that have roughly equal scores, as that can be an indication of a poor quality, low-value read. Such unaligned reads can be post-processed to contig and sent separately as a supplement. (See e.g., Reference 9).

Exemplary Data analysis and interpretation: The exemplary implementation can be evaluated on five tumor data-sets at several coverages (e.g., about 30×-1000×), with each dataset presented in terms of fluorescence intensity values. Each test can simulate a data transmission step, in which a sender computes the edit-calls from the BAM files using an independent base-calling procedure (e.g., Bustard) and also sends the compressed output of TRC (e.g., after it has been applied to the intensity files). The receiver does the same from the synthetic BAM files after decompression with TRC. The edit-calls computed by the sender can be compared against those computed by the receiver and can be examined for concordance and error statistics (e.g., false positives and negatives using ROC curves). Compressibility can be reduced by including further background knowledge available for each such clinical application (e.g., by including important disease-related SNPs and other tunable components augmented with known variants). If TRC has too many false negatives because of a high weight to the reference genome, then the weight can be reduced. This can increase the rate of false positives but, with higher coverage, these false-positives can be eliminated. In addition, the exemplary TRC can be modified to include information about known panels of disease-related SNP's, which can ensure that such SNPs can be sampled with enough coverage to rule out false positives. It can be important to note that TRC may not be platform specific and, TRC can be modified to accommodate other types of sequencing platforms besides Illumina (e.g., Ion Torrent, for instance) by using those systems' analog signals in place of the fluorescence intensity data generated by Illumina machines.

The exemplary procedure TRC alleviates these problems. To reduce analysis time and complexity, it can combine the functions of multiple downstream bioinformatics tools (e.g., error correction, alignment, non-interpreted variant calling) into one module, performing analysis on-the-fly versus during post-sequencing as is the current practice. TRC can introduce two pipeline functions: (i) extensive data compression and (ii) encryption tailored to clinical sequencing. The result can be faster delivery of more accurate data to clinicians and patients, drastically reducing the risks and costs of storage and transfer. These capabilities can uniquely open the sequencing field to smaller hospitals and labs where security, transfer and storage costs were previously barriers to entry.

Exemplary Reference-Based Compression

Reference-based compression operates by replacing base-by-base sequence "reads" with their coordinates (e.g., read-start and offset) in a common reference genome. Thus dramatically reducing the data footprint. Any differences from the reference, such as single nucleotide variations, insertions and deletions of short sequences, and unmappable reads can also be recorded. The exemplary implementation, of TRC, can achieve greater than about a 50:1 compression, surpassing the currently best-achievable compression. It can be possible to store approximately 30× coverage of the genome in less than about 1 GB of memory.

Further Exemplary Level of Security Comparable to the Currently-Best OpenpGP Standard The exemplary TRC can provide HIPAA level security, privacy and anonymity by encrypting the coordinates of variants before transmission using the OpenPGP public-key crypto-system. Since the variants and their chromosomal locations will be unknown to an eavesdropper, it will be impossible to interpret the data to find the identity of, or the mutations in, any individual's genome, because the mathematical problems underlying the public key system can be computationally intractable.

Figure 8:
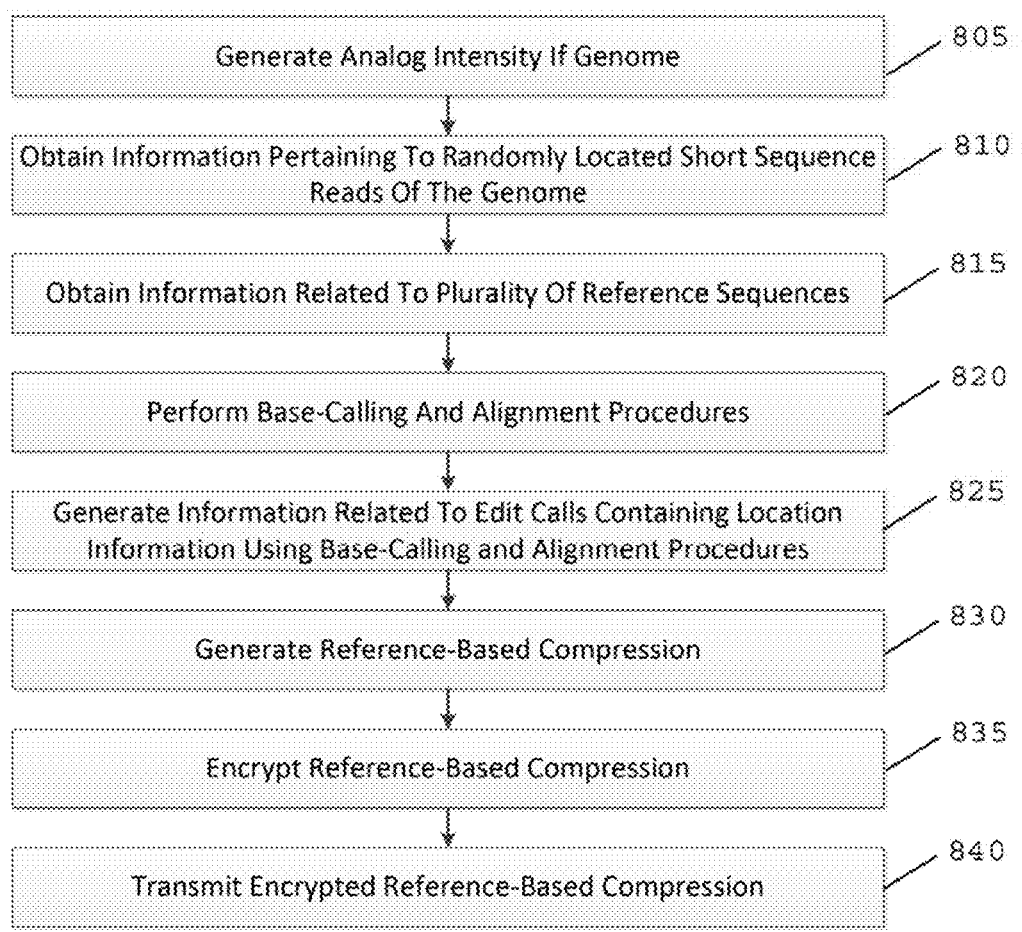
FIG. 8 is a flow diagram of an exemplary method for generating a reference-based compression of randomly located short sequence reads from a genome(s) according to an exemplary embodiment of the present disclosure.

FIG. 8 is a flow diagram of an exemplary method for generating a reference-based compression of randomly located short sequence reads from a genome(s) according to an exemplary embodiment of the present disclosure. For example, at procedure 805, an analog intensity of the genome can be generated. This, or other information pertaining to randomly located short sequence reads of the genome can be obtained at procedure 810. At procedure 815, information related to a plurality of reference sequences can be obtained. At procedure 820, base-calling and alignment procedures can be performed, and information related to edit calls containing location information can be generated using the base-calling and alignment procedures at procedure 825. At procedure 830, a reference-based compression of the genome can be generated, which can be encrypted at procedure 835. At procedure 840, the encrypted reference-based compression of the genome can be transmitted over a network.

Figure 9:
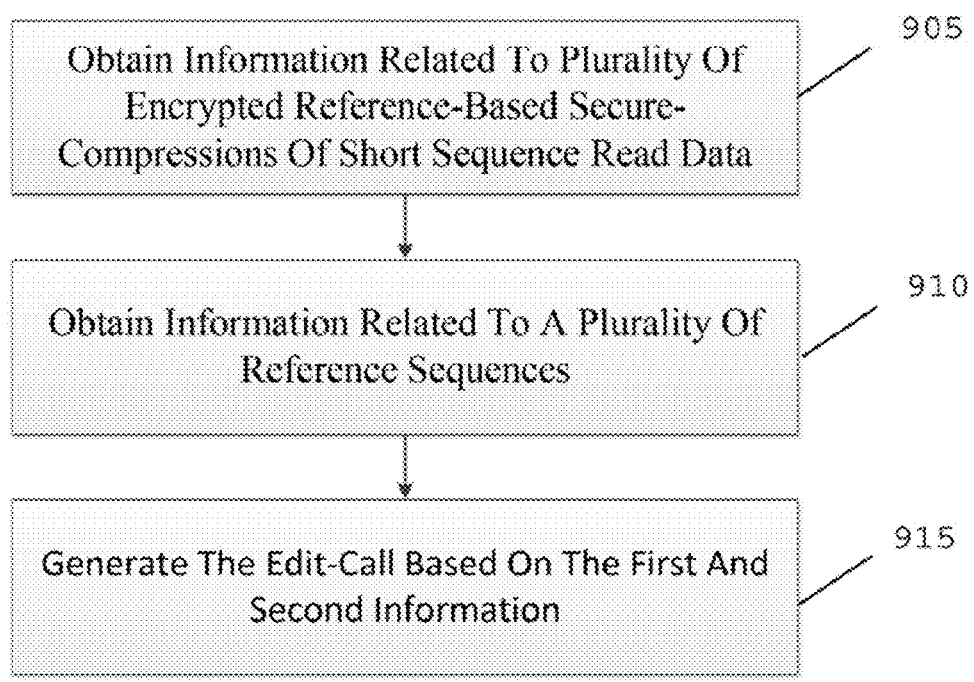
FIG. 9 is a flow diagram of an exemplary method for generating edit-call(s) including locational information according to an exemplary embodiment of the present disclosure.

FIG. 9 is a flow diagram of an exemplary method for generating edit-call(s) including locational information according to an exemplary embodiment of the present disclosure. For example, at procedure 905, information related to a plurality of encrypted references-based secure-compressions of short sequence reads can be obtained. At procedure 910, Information related to a plurality of reference sequences can be obtained. At procedure 915, edit-calls can be generated based on the information above.

Figure 10:
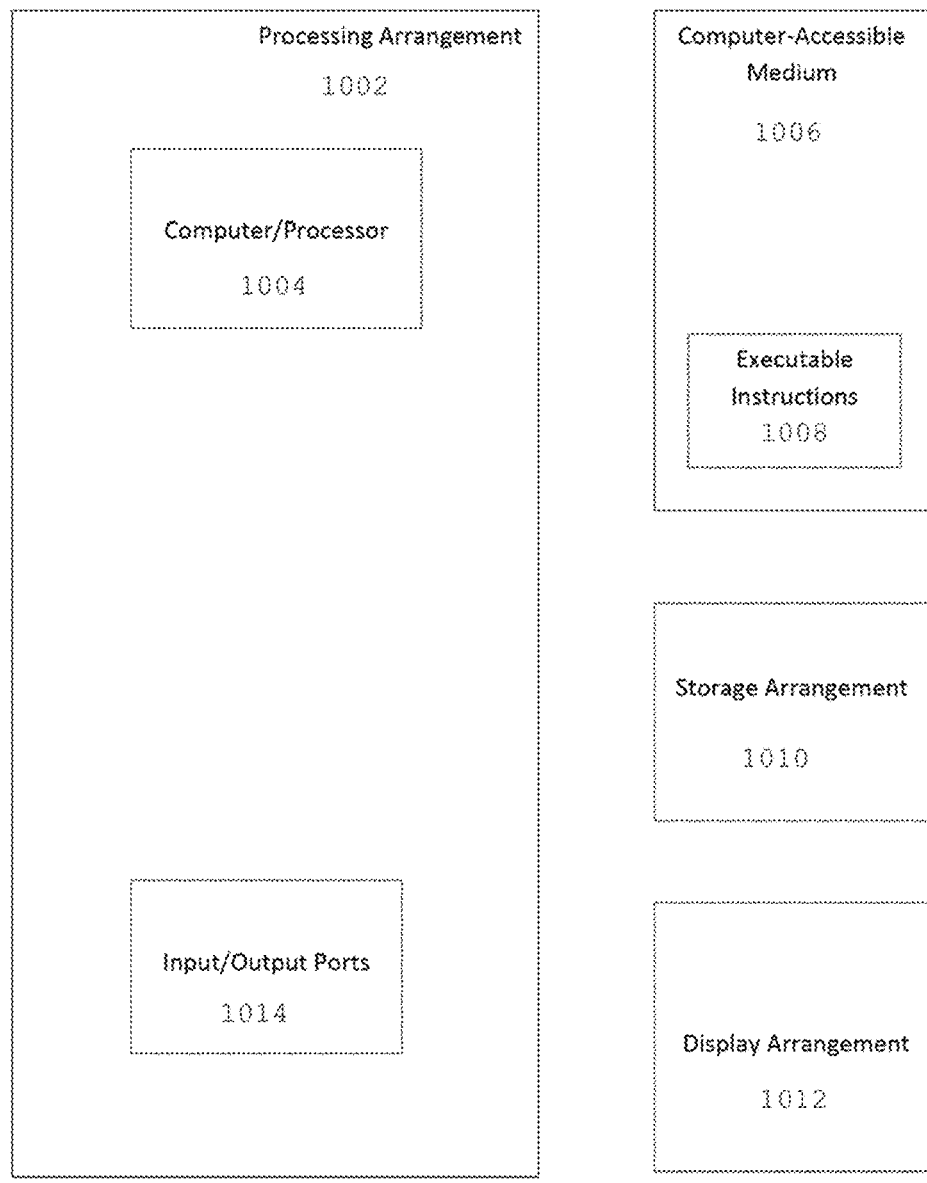
FIG. 10 is an illustration of an exemplary block diagram of an exemplary system in accordance with certain exemplary embodiments of the present disclosure.

FIG. 10 shows a block diagram of an exemplary embodiment of a system according to the present disclosure. For example, exemplary procedures in accordance with the present disclosure described herein can be performed by a processing arrangement and/or a computing arrangement 1002. Such processing/computing arrangement 1002 can be, for example entirely or a part of, or include, but not limited to, a computer/processor 1004 that can include, for example one or more microprocessors, and use instructions stored on a computer-accessible medium (e.g., RAM, ROM, hard drive, or other storage device).

As shown in FIG. 10, for example a computer-accessible medium 1006 (e.g., as described herein above, a storage device such as a hard disk, floppy disk, memory stick, CD-ROM, RAM, ROM, etc., or a collection thereof) can be provided (e.g., in communication with the processing arrangement 1002). The computer-accessible medium 1006 can contain executable instructions 1008 thereon. In addition or alternatively, a storage arrangement 1010 can be provided separately from the computer-accessible medium 1006, which can provide the instructions to the processing arrangement 1002 so as to configure the processing arrangement to execute certain exemplary procedures, processes and methods, as described herein above, for example.

Further, the exemplary processing arrangement 1002 can be provided with or include an input/output arrangement 1014, which can include, for example a wired network, a wireless network, the internet, an intranet, a data collection probe, a sensor, etc. As shown in FIG. 10, the exemplary processing arrangement 1002 can be in communication with an exemplary display arrangement 1012, which, according to certain exemplary embodiments of the present disclosure, can be a touch-screen configured for inputting information to the processing arrangement in addition to outputting information from the processing arrangement, for example. Further, the exemplary display 1012 and/or a storage arrangement 1010 can be used to display and/or store data in a user-accessible format and/or user-readable format.

The foregoing merely illustrates the principles of the disclosure. Various modifications and alterations to the described embodiments will be apparent to those skilled in the art in view of the teachings herein. It will thus be appreciated that those skilled in the art will be able to devise numerous systems, arrangements, and procedures which, although not explicitly shown or described herein, embody the principles of the disclosure and can be thus within the spirit and scope of the disclosure. Various different exemplary embodiments can be used together with one another, as well as interchangeably therewith, as should be understood by those having ordinary skill in the art. In addition, certain terms used in the present disclosure, including the specification, drawings and claims thereof, can be used synonymously in certain instances, including, but not limited to, for example, data and information. It should be understood that, while these words, and/or other words that can be synonymous to one another, can be used synonymously herein, that there can be instances when such words can be intended to not be used synonymously. Further, to the extent that the prior art knowledge has not been explicitly incorporated by reference herein above, it is explicitly incorporated herein in its entirety. All publications referenced are incorporated herein by reference in their entireties.

EXEMPLARY REFERENCES

The following references are hereby incorporated by reference in their entireties.

1. Rehm, H. L., S. J. Bale, P. Bayrak-Toydemir, J. S. Berg, K. K. Brown, J. L. Deignan, M. J. Friez, B. H. Funke, M. R. Hegde, E. Lyon, G. Amer Coll Med, and A. Genomics Lab Quality, *ACMG clinical laboratory standards for next-generation sequencing*. Genetics in Medicine, 2013. 15(9): p. 733-747.
2. Schrijver, I., N. Aziz, D. H. Farkas, M. Furtado, A. F. Gonzalez, T. C. Greiner, W. W. Grody, T. Hambuch, L. Kalman, J. A. Kant, R. D. Klein, D. G. B. Leonard, I. M. Lubin, R. Mao, N. Nagan, V. M. Pratt, M. E. Sobel, K. V. Voelkerding, and J. S. Gibson, *Opportunities and Challenges Associated with Clinical Diagnostic Genome Sequencing A Report of the Association for Molecular Pathology*. Journal of Molecular Diagnostics, 2012. 14(6): p. 525-540.
3. Shoenbill, K., N. Fost, U. Tachinardi, and E. A. Mendonca, *Genetic data and electronic health records: a discussion of ethical, logistical and technological considerations*. Journal of the American Medical Informatics Association, 2014. 21(1): p. 171-180.
4. *NSF Innovation Corps*. Available from: http://www.nsf.gov/news/special_reports/i-corps/index.jsp.
5. Menges, F., G. Narzisi, and B. Mishra, *TotalReCaller: improved accuracy and performance via integrated alignment and base-calling*. Bioinformatics, 2011. 27(17): p. 2330-2337.
6. Fritz, M. H. Y., R. Leinonen, G. Cochrane, and E. Birney, *Efficient storage of high throughput DNA sequencing data using reference-based compression*. Genome Research, 2011. 21(5): p. 734-740.
7. Deorowicz, S. and S. Grabowski, *Data compression for sequencing data*. Algorithms for Molecular Biology, 2013.
8. Masys, D. R., G. P. Jarvik, N. F. Abernethy, N. R. Anderson, G. J. Papanicolaou, D. N. Paltoo, M. A. Hoffman, I. S. Kohane, and H. P. Levy, *Technical desiderata for the integration of genomic data into Electronic Health Records*. Journal of Biomedical Informatics, 2012. 45(3): p. 419-422.
9. Li, H., B. Handsaker, A. Wysoker, T. Fennell, J. Ruan, N. Homer, G. Marth, G. Abecasis, R. Durbin, and P. Genome Project Data, *The Sequence Alignment/Map format and SAMtools*. Bioinformatics, 2009. 25(16): p. 2078-2079.
10. Corporation, O., *A Performance Evaluation of Storage and Retrieval of DICOM Image Content in Oracle Database 11 g Using HP Blade Servers and Intel Processors*, 2010.
11. Bisiani, R., *Beam Search*, in *Encyclopedia of Artificial Intelligence* 1987, Wiley & Sons. p. 56-58.
12. Land, A. and A. Doig, *An Automatic Method of Solving Discrete Programming Problems*. Econometrica, 1960. 28(3): p. 497-520.
13. Systems, S. MARS. Available from: http://www.salford-systems.com/products/mars.
14. DICOM. Available from: http://dicom.nema.org/.
15. HL7. Available from: http://www.hl7.org/.
16. Open PGP. Available from: http://www.pa.msu.edu/reference/pgpdoc1.html.

What is claimed is:

1. A non-transitory computer-accessible medium having stored thereon computer-executable instructions for generating at least one compressed genetic sequence, wherein, when a computer arrangement executes the instructions, the computer arrangement is configured to perform procedures comprising:
   (a) obtaining at least one reference sequence;
   (b) obtaining a particular sequence read for at least one genetic sequence from a sequence platform;
   (c) comparing the particular sequence read to the at least one reference sequence;
   (d) storing the particular sequence read only if the particular sequence read does not match the at least one reference sequence; and
   (e) generating the at least one compressed genetic sequence by repeating procedures (b)-(d) for further sequence reads which are different from the particular sequence read.

2. The computer-accessible medium of claim 1, wherein the computer arrangement is further configured to store location information for the particular sequence read only if the particular sequence read does not match the at least one reference sequence.

3. The computer-accessible medium of claim 2, wherein the computer arrangement is further configured to encrypt the location information.

4. The computer-accessible medium of claim 3, wherein the computer arrangement is configured to encrypt the location information using a public-key crypto procedure.

5. A method for generating at least one compressed genetic sequence, comprising:
   (a) obtaining at least one reference sequence;
   (b) obtaining a particular sequence read for at least one genetic sequence from a sequence platform;
   (c) comparing the particular sequence read to the at least one reference sequence;
   (d) storing the particular sequence read only if the particular sequence read does not match the at least one reference sequence; and
   (e) using a computer hardware arrangement, generating the at least one compressed genetic sequence by repeating procedures (b)-(d) for further sequence reads which are different from the particular sequence read.

6. The method of claim 5, further comprising storing location Information for the particular sequence read only if the particular sequence read does not match the at least one reference sequence.

7. The method of claim 6, wherein further comprising encrypting the location information.

8. The method of claim 7, wherein the encryption of the location information is performed using a public-key crypto procedure.

9. A system for generating at least one compressed genetic sequence, comprising:
   a computer hardware arrangement configured to:
   (a) obtaining at least one reference sequence;
   (b) obtaining a particular sequence read for at least one genetic sequence from a sequence platform;
   (c) comparing the particular sequence read to the at least one reference sequence;
   (d) storing the particular sequence read only if the particular sequence read does not match the at least one reference sequence; and
   (e) generating the at least one compressed genetic sequence by repeating procedures (b)-(d) for further sequence reads which are different from the particular sequence read.

10. The system of claim 9, wherein the computer hardware arrangement is further configured to store location information for the particular sequence read only if the particular sequence read does not match the at least one reference sequence.

11. The system of claim 10, wherein the computer hardware arrangement is further configured to encrypt the location information.

12. The system of claim 11, wherein the computer hardware arrangement is configured to encrypt the location information using a public-key crypto procedure.

* * * * *